United States Patent [19]

Blackburn

[11] Patent Number: 4,468,965

[45] Date of Patent: Sep. 4, 1984

[54] TEST METHOD FOR ACETYLENE CYLINDERS

[75] Inventor: Philip R. Blackburn, Lewiston, N.Y.

[73] Assignee: Union Carbide Corporation, Danbury, Conn.

[21] Appl. No.: 439,634

[22] Filed: Nov. 5, 1982

[51] Int. Cl.³ .......................................... G01N 29/04
[52] U.S. Cl. ........................................ 73/587; 73/801
[58] Field of Search ............................... 73/587, 801

[56] References Cited

U.S. PATENT DOCUMENTS

| | | | |
|---|---|---|---|
| 3,545,262 | 12/1970 | Steele et al. | 73/88.5 |
| 3,713,127 | 1/1973 | Keledy et al. | 340/261 |
| 3,919,883 | 11/1975 | Nakamura et al. | 73/71.4 |
| 4,033,179 | 7/1977 | Romrell | 73/71.4 |
| 4,036,057 | 7/1977 | Morais | 73/88 R |
| 4,201,092 | 5/1980 | Dau | 73/587 |

FOREIGN PATENT DOCUMENTS 55-89745  7/1980  Japan ....................................... 73/587

OTHER PUBLICATIONS

Harris, D. O. and Dunegan, H. L., Verification of Structural Integrity of Pressure Vessels by Acoustic Emission and Periodic Proof Testing, ASTM STP 515, pp. 158-170, 1972.

Green, A. T., Acoustic Emission Testing, TEST, pp. 8-17, Oct./Nov. 1978.

Primary Examiner—Anthony V. Ciarlante
Attorney, Agent, or Firm—Stanley Ktorides

[57] ABSTRACT

Integrity of acetylene cylinder filler material is accurately and easily determined by monitoring acoustic emission counts as a function of load and establishing the distinctive signature of faulty filler material.

9 Claims, 3 Drawing Figures

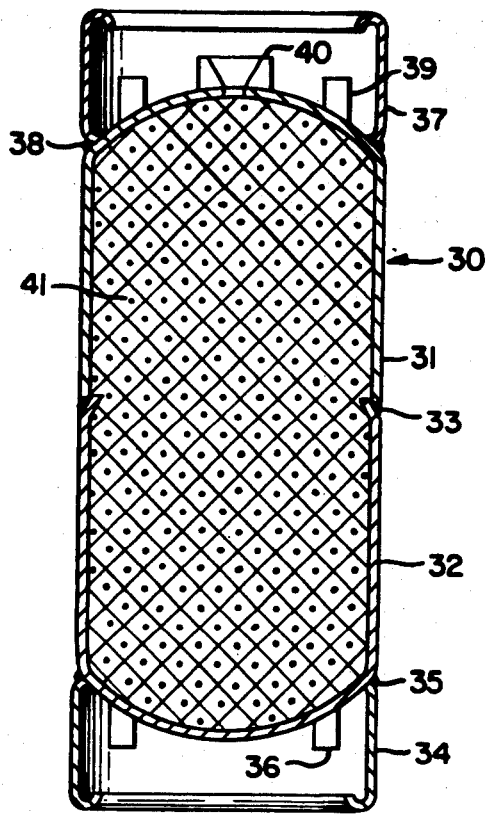
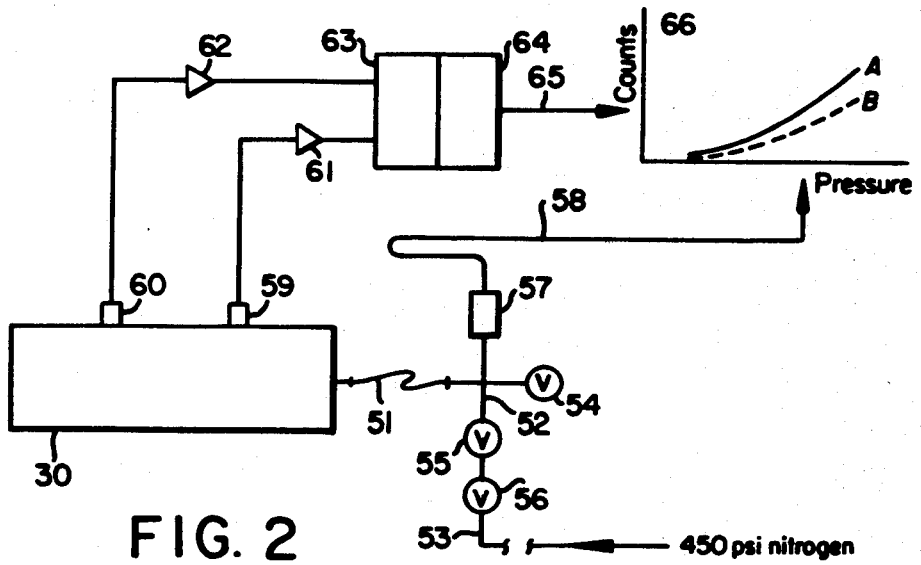
FIG. 1
FIG. 2

TEST METHOD FOR ACETYLENE CYLINDERS

TECHNICAL FIELD

This invention relates generally to the field of non-destructive testing and more particularly to the field of non-destructive testing by monitoring acoustic emission.

BACKGROUND ART

Acetylene gas is widely used in many applications such as metal working operations. Generally acetylene gas is provided to the use point in cylinders which are filled at a central filling location and distributed to the use point. When the acetylene gas in the cylinder has been completely used up at the use point, the empty cylinder is returned to the central filling location for refilling.

As is well known, acetylene gas is very dangerous and unstable, and is highly susceptible to violent decomposition from an incidental energy input such as heat or mechanical impact. For this reason an acetylene gas cylinder has some important differences from a typical gas cylinder such as an oxygen cylinder. Whereas a typical gas cylinder is hollow inside, an acetylene gas cylinder is characterized by a filler material which fills the inside of the cylinder. The filler material is introduced into the cylinder as a slurry and heat treated to form solidified porous filler material throughout the interior cavity. Typically the filler material has a void space of about 90 percent of the cylinder interior. Often the filler material is a mixture of silica, lime and asbestos. Other suitable filler materials include a charcoal monolithic material made of charcoal, Portland cement and Kieselguhr.

When the acetylene gas cylinder is to be charged with acetylene it is first charged with a liquid solvent, such as acetone. Then the acetylene gas is charged into the cylinder under pressure and is dissolved in the solvent until it is needed for use. In this way, the acetylene gas is not allowed to build up as a gas within the cylinder and is thus much safer to transport and store.

It is important that the filler material retain its integrity throughout the life of the cylinder. A crack or large void in the filler material can allow a dangerous buildup of acetylene gas to occur. However, as can be appreciated it is quite difficult to determine the integrity of the filler material since it cannot be visually inspected. Tests to determine the integrity of acetylene cylinder filler material are generally expensive, time consuming or not very reliable. Thus it is desirable to provide an inexpensive test procedure to quickly and accurately determine the integrity of acetylene cylinder filler material.

A known method to detect cracks and other flaws in structures, such as pressure vessels, is acoustic emission testing which is based on the principle that a crack or other flaw in a structure will enlarge as a load is applied to the structure and that such enlargement will release energy partly in the form of stress waves which can be sensed and recorded. In the case of pressure vessels a typical acoustic emission test comprises filling the pressure vessel with a pressurizing fluid, such as a gas, and sensing the acoustic emission events which occur in the vessel walls by means of sensors attached to the exterior walls. An acoustic emission event is generated by a sharp release of energy partly resolved as stress waves, as the force holding material together is broken. By measuring such events one can determine the condition of the pressure vessel walls.

Acoustic emission testing has two general characteristics which are of importance herein. The first is an essentially exponential or non-linear generation of acoustic emission counts with increasing load. The second is termed the "Kaiser effect" which is the non-reversibility of acoustic emission testing. Once a structure has been stressed to a given load and that load released, a subsequent loading will not generate acoustic emission until the previous maximum load has been exceeded. That is, once a flaw is caused to grow under stress so as to generate acoustic emission and that stress removed, the flaw will not return to its pre-stress condition and a subsequent application of stress will not cause the flaw to grow with consequent acoustic emission until the subsequent stress exceeds the previously applied stress. Therefore when one tests a structure by measuring acoustic emission one expects to get a non-linear relationship of acoustic emission to increasing load due to (a) the inherent nature of materials to exponentially release energy, as their failure point is approached and (b) the Kaiser effect wherein a pre-stressed flaw will not generate acoustic emission until the prior maximum loading on that flaw is exceeded.

Acoustic emission testing is a very versatile non-destructive testing technique. Although it would be desirable to employ acoustic emission testing to determine the integrity of acetylene cylinder filler material, of course, sensors cannot be placed on the filler material. Since the sensors must be placed on the cylinder shell, it is not evident that an accurate reading of acoustic emission specific to the filler material can be obtained.

It is therefore an object of this invention to provide an uncomplicated and inexpensive non-destructive test to determine the integrity of cylinder filler material and the consequent suitability of the cylinder for use.

It is another object of the invention to employ acoustic emission testing to accurately determine the integrity of cylinder filler material.

SUMMARY OF THE INVENTION

The above and other objects which will become obvious to one skilled in the art are attained by a method for determining the integrity of solidified porous filler material within a cylinder comprising:

(a) providing a cylinder having solidified porous filler material in its interior.

(b) adapting sensing means to the cylinder capable of sensing acoustic emission counts generated by pressurization of said cylinder;

(c) pressurizing the cylinder with a fluid to a desired pressure to generate acoustic emission counts;

(d) establishing a relationship of acoustic emission counts generated during step (c) as a function of increasing pressure;

(e) determining whether the relationship of acoustic emission counts to pressure established in step (d) is essentially a linear relationship; and (f) on the basis of the determination made in step (e), determining the integrity of the filler material within the cylinder.

As used herein, the term "acoustic emission" means impulsively-generated stress waves in a material.

As used herein, the term "acoustic emission count" means an acoustic emission level which is momentarily greater than a predetermined threshold.

As used herein, the term "porous" means having a void space or void fraction of from 50 to 99 percent, preferably from 75 to 95 percent.

As used herein, the term "cylinder" means any vessel designed to hold a fluid at pressure and is not limited to a vessel having a cylindrical shape.

As used herein, the term "pressurize" means to increase the pressure exerted on the inside surface of a cylinder over that exerted on the outside surface. A convenient way to pressurize a cylinder is to fill the interior of the cylinder with a fluid and increase the pressure on the fluid.

BRIEF DESCRIPTION OF THE DRAWINGS

FIG. 1 is a simplified diagram of a cross-section of a typical acetylene cylinder.

FIG. 2 is a diagram of one preferred setup useful in carrying out the method of this invention.

DETAILED DESCRIPTION

Figure 3:
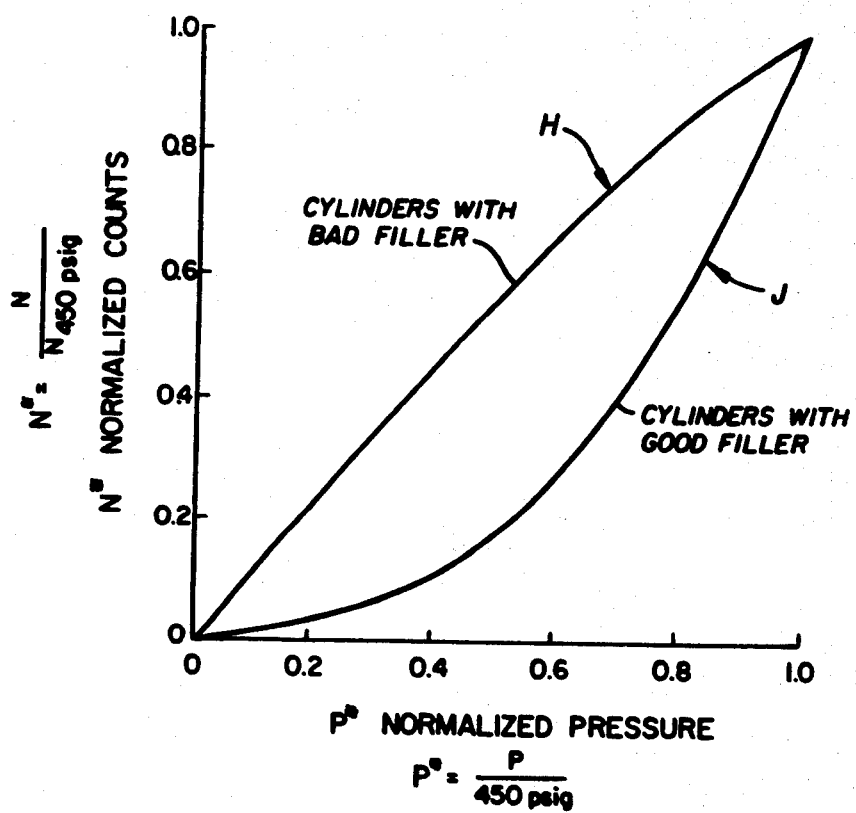
FIG. 3 is a graphical representation of normalized acoustic emission versus pressure curves for cylinders having bad and good filler material respectively.

This invention is based on the discovery that cylinders having faulty filler material exhibit a distinctive relationship of emission counts versus load which is different and contrary to that which would be predicted by acoustic emission testing theory and experience and also on the discovery that such a distinctive relationship or signature is specific to the determination of the condition of the filler material.

The test method of this invention will be described with reference to the drawings. FIG. 1 is a cross-sectional representation of a typical acetylene gas cylinder 30 having a steel shell in two parts, with top part 31 and bottom part 32 joined by girth weld 33. The cylinder is supported on bottom ring 34 which is welded to the shell as at 35. Top ring 37 is welded to the shell as at 38. These rings provide convenient handling and support means for the cylinders. The cylinder shell has top 39 and bottom 36 fuse plugs to guard against the buildup of pressure within the cylinder. The acetylene gas is charged and discharged through top block 40 which contains the necessary regulator and valve arrangements for such gas handling. The solidified porous filler material 41 fills the entire inside cavity of the cylinder. Although the FIG. 1 representation is typical, there could be a number of variations such as a one-piece shell.

Referring to FIG. 2, acetylene cylinder 30 is connected by flexible hose 51 to a suitable gas supply 53 such as high pressure nitrogen. The gas may be regulated through associated control valves including shutoff valve 56, throttle valve 55 and vent valve 54. The gas pressure is monitored by suitable pressure transmitter 57 which outputs that information to a recorder for data logging acoustic emission counts as a function of pressure 66. Two acoustic emission sensors (piezoelectric transducers) are attached to the cylinder outer wall at about one-third the distance from each end. The sensor may be held against the cylinder wall with hose clamps. Stopcock grease is a suitable acoustic coupling medium. Emission sensed by sensors 59 and 60 are sent as electrical signals to preamplifier 61 and 62 respectively and then to amplifier 63 and counter 64. The data from counter 64 is transmitted 65 to X-Y plotter 66 and recorded versus pressure as curves A and B. Although the set up shown in FIG. 2 is preferred there can be other arrangements which are suitable. For example, one need employ but one sensor or can employ more than the two illustrated in FIG. 2. All of the equipment shown and described in FIG. 2 is available commercially and those skilled in the art are familiar with the procurement and use of such equipment.

The pressurizing fluid may be any fluid which does not compromise the intended use of the cylinder. Preferably the pressurizing fluid is an inert gas such as nitrogen, argon and the like. Dry air may also be employed though it is not preferred with acetylene cylinders because of the oxygen component of the air. The pressurizing gas may also be the use gas and as such, the cylinder test can be carried out simultaneously with the charging of the cylinder.

In a typical test procedure, nitrogen gas is delivered to the cylinder to be tested at a rate of from 5 to 100 psi (pounds per square inch) per minute, preferably from 30 to 70 psi per minute until the pressure inside the cylinder has increased to about 450 psig. The cylinder may be pressurized to any desired pressure and the desired pressure will be dependent on many factors such as the pressure at which the pressurizing fluid is available and the time that one wishes to spend conducting the test. It is preferable that the desired pressure equal and most preferable that the desired pressure exceed by about 10 percent the use pressure, i.e., the pressure at which the cylinder normally operates or is intended to operate. Acoustic emission generated during the pressurization are sensed by one or both of the sensors and the sound energy is converted to an electrical signal. All signals which have an amplitude greater than a predetermined threshold are counted and recorded versus pressure. A threshold is employed in order to filter out extraneous noise. Typically the threshold level is about one volt.

Unexpectedly it has been found that cylinders having faulty filler material produce an acoustic emission count versus pressure relationship which is essentially linear rather than exponential and therefore is contrary to what one would expect based on theory and practice. This essentially linear relationship is a distinctive signature of faulty filler material and is present whether or not the cylinder shell itself is faulty. Thus this signature is specific to the filler material. This is that much more remarkable because the sensors must necessarily be attached to the cylinder wall and thus inherently must also sense acoustic emission generated by the cylinder wall. However this heretofore vexing problem of sensor placement has no effect upon the signature of the filler material and therefore no effect upon the accuracy of the test. A cylinder having acceptable filler material will generate a conventional exponential or non-linear acoustic emission count versus pressure relationship. Thus by generating an acoustic emission count versus pressure relationship for a cylinder, one can quickly determine the condition of the filler inside the cylinder. An essentially linear relationship is the distinctive sign of faulty filler while an essentially non-linear or exponential relationship indicates that the filler is intact and suitable for further use.

For a clearer indication of the relationship of emission counts to pressure reference is made to FIG. 3. Curve J is a curve representing normalized values of emission counts versus pressure for 5 cylinders having good filler material and curve H represents normalized values of emission counts versus pressure for 4 cylinders having faulty filler material. Each cylinder tested was pressurized to 450 psig at a rate of from 17 to 35 psi/minute. By "normalized" it is meant that the value at any point is divided by the maximum value. In this way a number of different cylinders can yield data which can be meaningfully compared. It is thus clearly seen that cylinders with faulty filler material consistently exhibit an emission count to pressure relationship which is essentially linear and those with good filler material consistently exhibit an exponential or non-linear relationship.

FIG. 3 may also be used to more clearly show what is meant by an essentially linear relationship. For purposes of this application an essentially linear relationship is one wherein the normalized count value at a normalized pressure value of 0.5 is from about 0.3 to 0.7. Referring to FIG. 3, curve J has a normalized count value of 0.19 at a normalized pressure of 0.5 while curve H has a normalized count value of 0.56 at this point.

This linear relationship was completely unexpected and not only cannot be explained by conventional acoustic emission testing theory but runs counter to the expectations of such theory. Furthermore this unexpected relationship is not a mere curiosity but serrendipitously can be effectively employed to determine the integrity of cylinder filler material independently of the condition of the cylinder shell.

Although not wishing to be held to any theory, applicant believes that the unusual relationship which has been discovered may be, in part, explained by the fact that much acoustic emission generated by the pressurization of a cylinder with faulty filler material may not be generated by flaw propogation as in conventional acoustic emission testing. Instead acoustic emission may be generated by pressurizing fluid flowing through passages which normally would not exist, and, while doing so, entraining particles which impact the cylinder wall. Since such acoustic emission is not caused by flaw propogation the emission counts do not start at a low number and increase non-linearly with pressure, as would acoustic emission counts generated by flaw propagations for the reasons explained previously. However, as emphasized, the above explanation is speculative and the actual reasons for the unusual behavior discovered and so advantageously employed may be quite different, in whole or in part, from that offered above.

The test procedure of this invention is particularly advantageous in testing cylinders which have been in service and need testing to determine their suitability for being returned to service. This is because flaws in a cylinder shell which has been in service at a pressure of, for example, 300 psig will not generate any acoustic emissions during a test until 300 psig is exceeded unless a new flaw has appeared since the last pressurization. Thus the difference between cylinders with good or bad fillers is highlighted to a greater degree. A new cylinder may have some flaws in its shell and these flaws will begin generating acoustic emission immediately with the start of pressurization. Thus for testing new cylinders it may be advisable to test the cylinder a second time shortly after the first test. During the second test the cylinder will exhibit the Kaiser effect with respect to flaws in its shell and thus acoustic emission at the lower pressures due to faulty filler material will be highlighted.

Another advantage of the test method of this invention is the ability to pressurize a cylinder containing porous filler at a fast rate of up to 100 psi/minute. Heretofore it has been felt that a slow rate of less than about 20 psi per minute was necessary in order to produce useful readings because too much noise is generated at pressurization rates exceeding 20 psi per minute. It has been found that acetylene cylinders having the interior filled with solidified porous filler material can be pressurized at much higher rates without sacrificing accuracy. This adds to the efficiency of the test. This high rate of pressurization can be employed when one is seeking to determine the structual integrity of the cylinder shell itself as well as when one wishes to determine the integrity of the filler material.

Although the test method of this invention has been described in detail with reference to a cylinder designed to hold acetylene gas, it is understood that the test method of this invention is equally applicable to any pressure vessel whose interior cavity contains solidified porous filler material.

I claim:

1. A method for determining the integrity of solidified porous filler material within a cylinder comprising:
   (a) providing a cylinder having solidified porous filler material in its interior;
   (b) adapting sensing means to the cylinder capable of sensing acoustic emission counts generated during pressurization of said cylinder;
   (c) pressurizing said cylinder with a fluid to a desired pressure to generate acoustic emission counts;
   (d) establishing a relationship of emission counts generated during step (c) as a function of increasing pressure;
   (e) determining whether the relationship of acoustic emission counts to pressure established in step (d) is essentially a linear relationship; and
   (f) on the basis of the determination made in step (e), determining the integrity of the filler material within the cylinder.

2. The method of claim 1 wherein said sensing means is attached to the outside shell of said cylinder.

3. The method of claim 1 wherein said fluid is an inert gas.

4. The method of claim 1 wherein said cylinder is pressurized at a rate of from 5 to 100 psi per minute.

5. The method of claim 1 wherein said cylinder is pressurized at a rate of from 20 to 100 psi per minute.

6. The method of claim 1 wherein said filler material has a void space of from 50 to 99 percent.

7. The method of claim 1 wherein said filler material comprises silica, lime and asbestos.

8. The method of claim 1 wherein said cylinder is constructed of steel.

9. The method of claim 1 wherein the relationship of emission counts to pressure is a normalized relationship.

* * * * *

UNITED STATES PATENT AND TRADEMARK OFFICE
CERTIFICATE OF CORRECTION

PATENT NO. : 4,468,965

DATED : September 4, 1984

INVENTOR(S) : P.R. Blackburn

It is certified that error appears in the above-identified patent and that said Letters Patent is hereby corrected as shown below:

In column 6, lines 4-18, delete "Another advantage of the test method of this invention is the ability to pressurize a cylinder containing porous filler at a fast rate of up to 100 psi/minute. Heretofore it has been felt that a slow rate of less than about 20 psi per minute was necessary in order to produce useful readings because too much noise is generated at pressurization rates exceeding 20 psi per minute. It has been found that acetylene cylinders having the interior filled with solidified porous filler material can be pressurized at much higher rates without sacrificing accuracy. This adds to the efficiency of the test. This high rate of pressurization can be employed when one is seeking to determine the structual integrity of the cylinder shell itself as well as when one wishes to determine the integrity of the filler material."

Signed and Sealed this

Twenty-fifth Day of December 1984

[SEAL]

Attest:

Attesting Officer

GERALD J. MOSSINGHOFF

Commissioner of Patents and Trademarks